United States Patent
Oumnia

(10) Patent No.: US 12,295,728 B2
(45) Date of Patent: May 13, 2025

(54) METHOD AND SYSTEM FOR ANALYSING THE USE OF AN ITEM OF FOOTWEAR

(71) Applicant: ZHOR TECH, Nancy (FR)

(72) Inventor: Karim Oumnia, Nancy (FR)

(73) Assignee: ZHOR TECH, Nancy (FR)

( * ) Notice: Subject to any disclaimer, the term of this patent is extended or adjusted under 35 U.S.C. 154(b) by 552 days.

(21) Appl. No.: 17/763,272

(22) PCT Filed: Sep. 24, 2020

(86) PCT No.: PCT/EP2020/076818
§ 371 (c)(1),
(2) Date: May 17, 2022

(87) PCT Pub. No.: WO2021/058698
PCT Pub. Date: Apr. 1, 2021

(65) Prior Publication Data
US 2022/0338735 A1 Oct. 27, 2022

(30) Foreign Application Priority Data

Sep. 24, 2019 (EP) .................................. 19306193.4
Apr. 14, 2020 (EP) .................................. 20169503.8

(51) Int. Cl.
*A61B 5/11* (2006.01)
*A61B 5/00* (2006.01)

(52) U.S. Cl.
CPC .......... *A61B 5/1121* (2013.01); *A61B 5/0022* (2013.01); *A61B 5/1112* (2013.01);
(Continued)

(58) Field of Classification Search
CPC ... A61B 5/0022; A61B 5/1112; A61B 5/1116; A61B 5/112; A61B 5/6807
See application file for complete search history.

(56) References Cited

U.S. PATENT DOCUMENTS 10,269,174 B2 * 4/2019 Torvinen ................. G06T 17/00
2014/0260677 A1 * 9/2014 Dojan ................ A63B 24/0062
  73/862.045

(Continued)

FOREIGN PATENT DOCUMENTS

EP  3199046 A1  8/2017

OTHER PUBLICATIONS

Translation of International Search Report & Written Opinion in PCT/EP2020/076818 dated Dec. 10, 2020, 9 pages.

*Primary Examiner* — Jonathan T Kuo

(57) ABSTRACT

The invention relates to a system for analyzing (1) the use of footwear items (11) configured to determine an association index between use parameter values (101) and shoe parameter values (201), said system a calculation computing device (30) configured for:
- Obtaining or loading posture or mobility parameter values (301) calculated from raw data generated by at least one connected sole (10);
- Obtaining or loading geographic parameter values (401) corresponding to a location of the at least one connected sole (10);
- Obtaining or loading shoe parameter values (201) including values of structural parameters, geometric parameters and/or aesthetic parameters of the footwear item (11);
- Calculating one or more use parameter values (101);
- Determining an association index value between the use parameter value(s) (101) and the shoe parameter values (201).

16 Claims, 3 Drawing Sheets

(52) U.S. Cl.
CPC ............. *A61B 5/1116* (2013.01); *A61B 5/112* (2013.01); *A61B 5/6807* (2013.01)

(56) References Cited

U.S. PATENT DOCUMENTS

| | | |
|---|---|---|
| 2015/0048942 A1 | 2/2015 | Bertagna et al. |
| 2015/0272264 A1 | 10/2015 | Lee |
| 2017/0213382 A1* | 7/2017 | Torvinen ................. A43B 3/34 |

\* cited by examiner

METHOD AND SYSTEM FOR ANALYSING THE USE OF AN ITEM OF FOOTWEAR

The invention relates to the field of footwear items and their design, the invention can find an application in the monitoring of daily or sporting activities, or else the monitoring of the physiological state of the subject of study so as to analyze a real use compared to a reference use of the footwear item.

PRIOR ART

In the space of fifty years, the use of the shoe has evolved considerably. Indeed, a few decades ago, the shoe was mainly used for its most basic function, that is to say a function of protection and support of the foot for daily movements and had to show a significant resistance to wear over time as highlighted in a study of the French shoe market carried out by J. Desabie and published in the journal of applied statistics, volume 2, n° 1 (1954), p. 69-82.

Growing health concerns are prompting individuals to engage in indoor and outdoor physical activities. Each of these activities can benefit from a footwear item with specific characteristics. In addition, the growing demand for novelty shoes is also a key driver for the global shoe industry. These footwear items generally have particular mechanical characteristics not necessarily related to the use that the user wishes to make of them. These trends have generated a strong growth in demand for shoes for all types of categories with, however, specific requirements depending on the destination, use of the footwear items. Thus, the number of shoe models with specific characteristics (mechanical characteristics, shape, structural composition of the different components of the shoe) for a given use has increased considerably in recent decades, whether this is related to a relaxation, formal, sports, medical, professional or more simply recreational use. In addition, to meet these growing needs, market players, in addition to analyzing uses and trends, are also focusing on the innovation and the development of new personalized products. The main companies operating in the market seek to improve the design of their shoes by allowing the user to provide them with data related to the morphology of their feet so that it best matches the user's foot.

Thus, the global shoe market can now be segmented by the type of shoes, final users of the shoes, various shoe selling platforms, materials used and their sales in various geographical regions. In order to identify new trends or else to determine the needs of users, nowadays, market studies are generally carried out quarterly and require the collection of a large amount of data, in particular related to the sale of shoe models, user feedbacks via satisfaction surveys, in order to be able to determine the needs of consumers. Thus, such studies have shown that the use of the shoe is no longer limited to the basic functions mentioned above. Indeed, whether in the context of health, or in the context of use in connection with sports practices or in the context of aesthetic preference, a wide range of shoes with very different technical characteristics are offered by the manufacturers. However, such studies are particularly difficult to carry out, since based in part on statistical analyses, they require sampling a very large number of people in order for the results of the study to be significant. It then becomes more and more laborious for shoe manufacturers, in view of the exponential growth of the shoe market and the number of shoe models and their use, to be able to identify trends related to the use of a specific type of shoe in a given context in order to develop new shoe models adapted to the needs of the user. The methods used in the context of these studies are only based on indirect and ad hoc analyzes of the needs or uses of users of footwear items. In addition, the information collected is generally fragmentary and does not allow the information to be contextualized.

Furthermore, manufacturers have also sought to develop clothing customization solutions accessible directly on their site from the Internet. A solution for personalizing sports clothing is described in particular in document EP3199046 and aims at combining data related to the user's gait (via the use of sensors) and the context in which the user practices a sport activity. By contextualizing the practice of certain sports, in particular the environment in which the sport is practiced, it is then possible to offer the user sports clothing that is best suited to the practice of his sport. However, such a solution does not allow to determine what use is made of the footwear item worn by the user or to determine a trend related to the evolution of the use of a type of footwear item.

Thus, the studies carried out, whether consumer studies or research and development studies, are based only on indirect, potentially subjective or biased information that cannot reflect what use is made of a footwear item by the population or determine a trend related to the evolution of the use of a type of footwear item.

There is therefore a need for a solution for analyzing the use of footwear items in order to determine what use is made of a footwear item by the population or else to determine a trend related to the evolution of the use of a type of footwear item.

TECHNICAL PROBLEM

The purpose of the invention is to overcome the disadvantages of the prior art. In particular, the aim of the invention is to propose a system for analyzing the use of footwear items allowing the determination of the use of a footwear item worn by a user in a given context in order, for example, to identify a trend of use of the footwear item.

BRIEF DESCRIPTION OF THE INVENTION

The invention relates to a system for analyzing the use of footwear items configured to determine an association index between use parameter values and shoe parameter values, mainly characterized by comprising a calculation computing device configured for:
- loading posture or mobility parameter values calculated from raw data generated by at least one connected sole of a footwear item;
- loading geographic parameter values, said geographic parameter values corresponding to a location of the at least one connected sole;
- loading shoe parameter values, said shoe parameter values comprising values of structural parameters, geometric parameters and/or aesthetic parameters of the footwear item including the at least one connected sole;
- calculating, for each connected sole, one or more use parameter values from the posture or mobility parameter values;
- determining, for each connected sole, an association index value between the use parameter values and the shoe parameter values.

In particular, the invention relates to a system for analyzing the use of footwear items configured to determine an association index between use parameter values and shoe parameter values, characterized in that it comprises one or more calculation computing devices configured for:

obtaining posture or mobility parameter values calculated from raw data generated by at least one connected sole of a footwear item;

obtaining geographic parameter values, said geographic parameter values corresponding to a location of the at least one connected sole;

obtaining shoe parameter values, said shoe parameter values including values of structural parameters, geometric parameters and/or aesthetic parameters of the footwear item including the at least one connected sole;

calculating, for each connected sole, one or more use parameter values from the posture or mobility parameter values; and determining, for each connected sole, an association index value between the use parameter value(s) and the shoe parameter values.

Such a system allows to determine the use made of a footwear item by a given user based in particular on the monitoring of his gait through at least one connected sole equipping the footwear item. The data relating to the user's gait are associated with location data of the connected sole in order to be able to segment the retrieved data for a determined geographical area. It is thus possible to determine the use made by a user of a particular footwear item from the data generated by the connected sole equipping the footwear item. This allows to highlight an association between a footwear item, originally designed by a manufacturer for a given activity, and the use that is actually made of it by the user of the footwear item. The manufacturer can thus have access to previously inaccessible data, allowing him to optimize the technical characteristics of a footwear item in line with the use made of it by the user. Thus, he will be able to easily access the behavior of users to serve them more personally and on a large scale.

According to other features of the system for analyzing the use of footwear items, said system may optionally include one or more of the following features, alone or in combination:

the calculation computing device is further configured to obtain plantar morphology parameter values of users of the connected sole and the association index values of these users are correlated with the plantar morphology parameter values. Thus it is possible to establish correlations between certain plantar morphology observed in the population and trends in the use of footwear items. Such comparisons can then be used to design footwear items that are particularly suitable for a group of users with similar plantar morphology.

the shoe parameter values include reference use parameters, the calculation computing device is further configured to identify a conventional and/or unconventional use, said identification including a comparison of the reference use parameters to the use parameter value calculated from the posture or mobility parameter values for each connected sole. This advantageously allows to determine in what way the user uses the footwear item. Depending on the footwear item in question, the latter may be intended for a certain type of activity, activity which may be characterized by values of reference posture or mobility parameters thus defining a reference use parameter for the footwear item. Thus, the calculated parameter value allows to describe a degree of correspondence between the use made by the user of the footwear item and a predetermined reference use.

the calculation computing device is further configured to calculate a global association index value from all the association index values previously determined for each connected sole. This advantageously allows to determine, for a set of connected soles considered in connection with a model of footwear items worn by a plurality of users, a value describing the use of the given model of footwear items for the set of connected soles and therefore of the users considered.

the calculation computing device is further configured to identify a trend, for a predetermined geographical area, from the global association index value correlated with the geographical parameter values of the at least one connected sole. This allows to determine a value describing the use of a given model of footwear items for a set of users considered for a given geographical area. Thus, the emergence of trends related to a particular use of a model of footwear items, within a city or a country can for example be highlighted. Furthermore, the geographical parameter values may further include meteorological values. Thus, uses according to meteorological conditions or uses not adapted to certain conditions (e.g. grip value not adapted to the presence of icy ground) can be highlighted.

the posture or mobility parameter values, the geographical parameter values, the shoe parameter values, the use parameter values and the association index values are associated with a unique identifier of the connected sole. This allows to structure all the data coming from or associated with a predetermined connected sole. It is thus possible to form a history of this data, for each connected sole, and thus to follow the evolution of the data resulting from or associated with each connected sole of a footwear item over time.

the geographical parameter values are generated and transmitted, to the calculation computing device, by the connected sole. This advantageously allows to dispense with the use of a third-party computing device, such as for example a smartphone or more generally a connected object, to generate the geographical parameter values, thus avoiding the problems associated with the coupling, via a short-range communication, from the connected sole to the third-party computing device through a dedicated application, which may reduce the autonomy of the energy source of the connected sole.

the calculation computing device is further configured to identify a plurality of connected soles, each being associated with another footwear item having shoe parameters that are substantially identical to the previously loaded shoe parameter values. This advantageously allows to collect a greater number of data and increases the significance of the parameter values produced. Indeed, it is thus possible to take into consideration the data generated or associated with connected soles of other models of footwear items, in particular models predestined for a use substantially identical to that of the connected sole whose shoe parameter values have been preloaded.

the calculation computing device is further configured to identify a plurality of third-party connected soles, each being associated with another footwear item having posture or mobility parameters substantially identical to the posture or mobility parameter values previously loaded. This advantageously allows to collect a greater number of data and increases the significance of the parameter values produced. Indeed, it is thus possible to take into consideration the data generated or associated with connected soles of other models of footwear items, in particular models predestined or not for a use substantially identical to that of the connected sole the posture or mobility parameter values of which have been previously loaded.

the calculation computing device is further configured to generate design parameters of the footwear item on the basis of the determined association index values between the use parameter values and the shoe parameter values. This advantageously allows to generate a personalized digital model from the shoe parameter values of the footwear item associated with the connected sole and to generate design parameters from said shoe parameter values taking into account the use made by the user of the footwear item.

The calculation computing device is further configured to generate production parameters relating to the manufacture of footwear items on the basis of the determined association index values between the use parameter values and the shoe parameter values. This advantageously allows to determine, from the shoe parameter values of the footwear item associated with the connected sole and taking into account the use made by the user of the footwear item, which materials must be used according to of the different parts forming the footwear item.

the calculation computing device is further configured to generate values of logistics parameters relating to the manufacture and distribution of footwear items on the basis of the geographical parameter values, the determined association index values between the use parameter values and the shoe parameter values. This advantageously allows to determine, from the shoe parameter values of the footwear item associated with the connected sole and by taking into account the use made by the user of the footwear item, a shipment route and transport means adapted for the distribution of footwear items in accordance with the use of the user and according to his geographical position.

the calculation computing device is further configured to receive wear parameter values of the footwear item associated with the connected sole and to generate production parameters relating to the manufacture of footwear items on the basis of the determined association index values, shoe parameter values and wear parameter values. These wear parameter values can come from the connected sole or from the presentation device(s) associated with the connected sole. The computing device can in particular receive wear parameter values from several connected soles used in different geographical areas. Thus, it is possible to provide for production cycles according to the use and even unexpressed needs of users.

According to another aspect, the invention relates to a method for analyzing the use of footwear items to determine an association index between use parameters and shoe parameters, said method being implemented by a calculation computing device and characterized in that said method comprises:

a step of loading posture or mobility parameter values calculated from raw data generated by at least one connected sole of a footwear item;

a step of loading geographic parameter values, said geographic parameter values corresponding to a location of the at least one connected sole;

a step of loading shoe parameter values, said shoe parameter values including values of structural parameters, geometric parameters and/or aesthetic parameters of the footwear item comprising the at least one connected sole;

a step of calculating, for each connected sole, one or more use parameter values from the posture or mobility parameter values;

a step of determining, for each connected sole, an association index value between the use parameter values and the shoe parameter values.

In particular, the invention relates to a method for analyzing the use of footwear items to determine an association index between use parameters and shoe parameters, said method being implemented by a calculation computing device and characterized in that said method comprises:

A step of obtaining posture or mobility parameter values calculated from raw data generated by at least one connected sole of a footwear item;

A step of obtaining geographic parameter values, said geographic parameter values corresponding to a location of the at least one connected sole;

A step of obtaining shoe parameter values, said shoe parameter values including values of structural parameters, geometric parameters and/or aesthetic parameters of the footwear item including the at least one connected sole;

A step of calculating, for each connected sole, one or more use parameter values from the posture or mobility parameter values; and A step of determining, for each connected sole, an association index value between the use parameter value(s) and the shoe parameter values.

Such a method allows to determine the use made of a footwear item by a given user based in particular on the monitoring of his gait through at least one connected sole equipping the footwear item. The data relating to the user's gait are associated with location data of the connected sole in order to be able to segment the data retrieved for a specific geographical area. It is thus possible to determine the use made by a user of a particular footwear item from the data generated by the connected sole equipping the footwear item. This allows to highlight an association between a footwear item, originally designed by a manufacturer for a given activity, and the use that is actually made of it by the user of the footwear item. The manufacturer can thus have access to previously inaccessible data, allowing him to optimize the technical characteristics of a footwear item in line with the use made of it by the user.

Depending on other characteristics of the method for analyzing the use of footwear items, the latter may optionally include one or more of the following characteristics, alone or in combination:

the shoe parameter values include reference use parameters and in that said method comprises a step of identifying a conventional and/or unconventional use, said identification including a comparison of the reference use parameters to the use parameter value calculated from the posture or mobility parameter values for each connected sole. This advantageously allows to determine how the user uses the footwear item. Depending on the footwear item in question, the latter may be intended for a certain type of activity, activity which may be characterized by values of reference posture or mobility parameters thus defining a reference use parameter for the footwear item. Thus, the calculated use parameter value allows to describe a degree of correspondence between the use made by the user of the footwear item and a predetermined reference use.

- it comprises a step of calculating a global association index value from all the association index values previously determined for each connected sole. This advantageously allows to determine, fora set of connected soles considered in connection with a model of footwear items worn by a plurality of users, a value describing the use of the given model of footwear items for the set of connected soles and therefore the users considered.
- it comprises a step of identifying a trend, for a predetermined geographical area, from the value of the global association index correlated with the geographical parameter values of the at least one connected sole. This allows to determine a value describing the use of a given model of footwear items for a set of users considered for a given geographical area. Thus, the emergence of trends related to a particular use of a model of footwear items, within a city or a country can for example be highlighted.
- the posture or mobility parameter values have been calculated by one or more processors integrated into the at least one connected sole. This allows to secure the data relating to the gait of users of connected soles and also to reduce the resource requirements for the systems for analyzing the use of footwear items.

Other advantages and characteristics of the invention will appear upon reading the following description given by way of illustrative and non-limiting example, with reference to the appended Figures which show:

DESCRIPTION OF THE INVENTION

Figure 1:
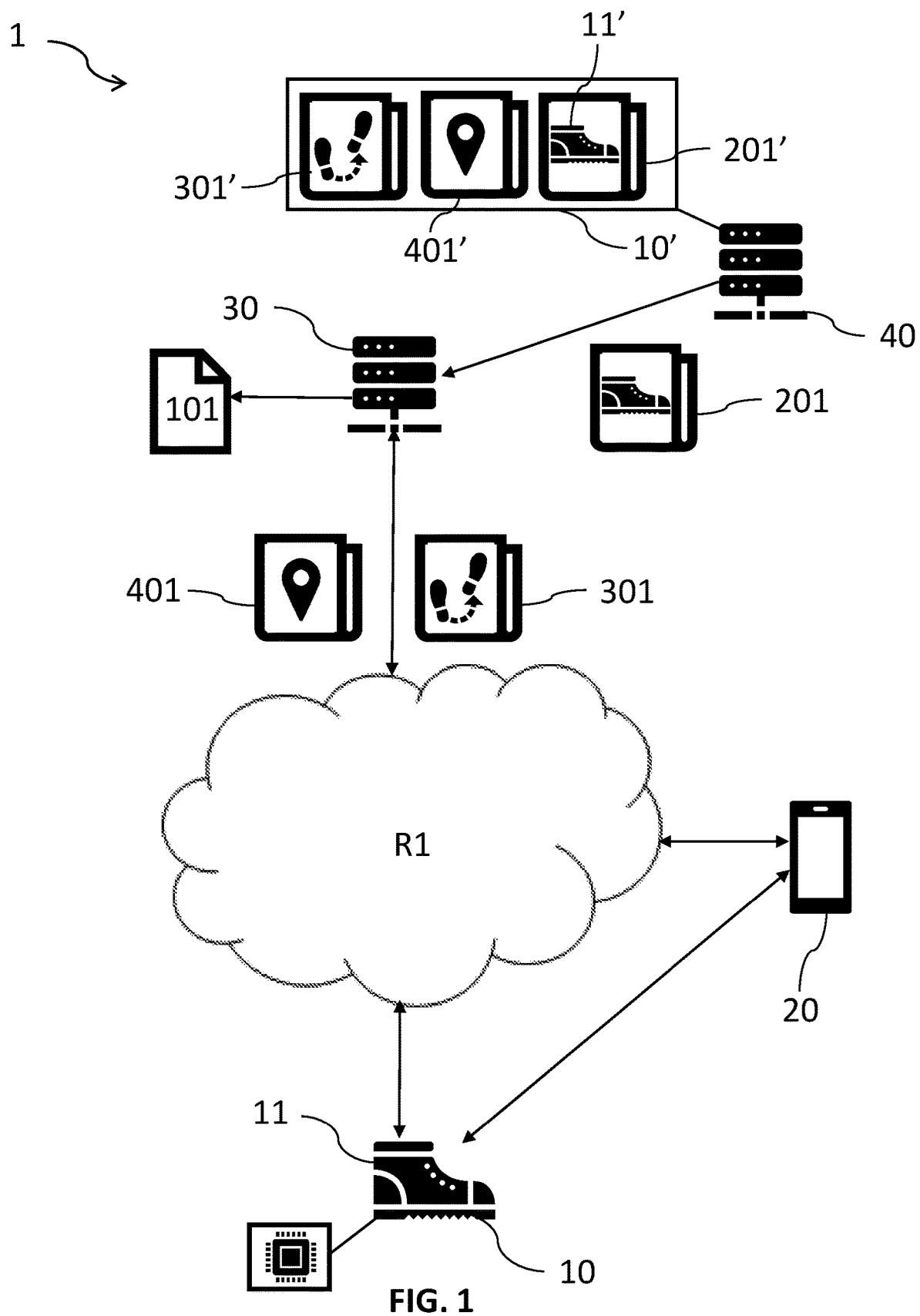
FIG. 1 shows a system for analyzing the use of footwear items according to one embodiment of the invention.

In the remainder of the description, "mobility" or "gait" within the meaning of the invention corresponds to the posture, movements, locomotion, and balance of the user. Balance corresponds in particular to postural balance related to the stability of the body and more particularly to the stability of a user's center of gravity. Nevertheless, it can integrate both static and dynamic balance.

The expression "mobility or posture parameters" or "gait parameter" corresponds to biomechanical parameters identified in the static or dynamic position of a person, a characteristic of a person's posture or mobility. A biomechanical parameter can be determined by various calculation operations from parameter values generated by sensors of a connected sole.

The expression "movement analysis", "mobility analysis" or "gait analysis" corresponds to the determination of a user's gait descriptor. It may correspond, within the meaning of the invention, to the attribution of one or more values, for example a score, a classification or a rating to a trajectory or to the displacement of a foot of a user. This characterization of the gait can allow to obtain one or more numerical or alphanumeric values of biomechanical parameters representative of the gait.

"Raw data" means data generated by sensors positioned in a connected sole, raw data can thus come from an inertial unit, a gyroscope, an accelerometer and a magnetometer for example. Raw data are usually generated for a given period of time and based on a user's gait.

"Bio-mechanical parameter" means within the meaning of the invention a characteristic of the posture or mobility of the user. "Advanced bio-mechanical parameter" means, within the meaning of the invention, a characteristic of the posture or mobility of the user determined at a key moment in a cycle and therefore more complex to be determined. A cycle being able for example to be a walking cycle. There are different types of activities such as pace, climbing a step, descending a step, stride, jump, flat, droop, stomp, kneel . . . . Therefore, a cycle can also correspond to a plurality of activities of different types depending on the complexity of the movement performed by the user.

"Substantially identical" within the meaning of the invention means a value varying by less than 30% with respect to the compared value, preferably by less than 20%, even more preferably by less than 10%.

"Sole" means an object allowing to separate the user's foot from the ground. A shoe can include an upper sole layer in direct contact with the foot of the user and a lower sole layer in direct contact with the ground or more generally the external environment. A shoe may also include a removable inner sole.

"Removable" means the ability to be easily detached, removed or disassembled without having to destroy the fastening means either because there is no fastening means or because the fastening means are easily and quickly removable (e.g. notch, screw, tab, lug, clips). For example, by removable, it should be understood that the object is not fixed by welding or by any other means not intended to allow the object to be detached.

"Process", "calculate", "determine", "display", "transform", "extract", "compare" or more broadly "executable operation" mean, within the meaning of the invention, an action performed by a device or processor unless the context indicates otherwise. In this regard, operations refer to actions and/or processes of a data processing system, for example a computing system or an electronic computing device, which manipulates and transforms data represented as physical (electronic) quantities in computing system memories or other information storage, transmission or display devices. These operations can be based on applications or software.

The term "learning" within the meaning of the invention corresponds to a method designed to define one or more correspondences, which may or may not take the form of a function f, allowing to calculate a value of Y from a base of n labeled (X1 . . . n, Y1 . . . n) or unlabeled (X1 . . . n) observations. Such a correspondence or function may correspond to a prediction model. Learning can be said to be supervised when it is based on labeled observations and unsupervised when it is based on unlabeled observations. In the context of the present invention, learning is advantageously used for determining an association index between use parameters and shoe parameters or else for generating production parameters relating to the manufacture of footwear items.

"Prediction model" means any mathematical model that allows to analyze a volume of data and to establish relationships between factors allowing the assessment of risks or that of opportunities associated with a specific set of conditions, in order to guide decision-making towards a specific action.

The terms or expressions "application", "software", "program code", and "executable code" mean any expression, code or notation of a set of instructions, intended to cause data processing to perform a particular function directly or indirectly (e.g. after a conversion operation to another code). The examples of program code may include, but is not limited to, a subroutine, function, an executable application, a source code, an object code, a library, and/or any other sequence of instructions designed for the running on a computing system.

The term "processor", within the meaning of the invention, means at least one hardware circuit configured to execute operations according to instructions contained in a code. The hardware circuit may be an integrated circuit. Examples of a processor comprise, but are not limited to, a central processing unit, a graphics processor, an application-specific integrated circuit (ASIC), and a programmable logic circuit.

"Coupled", within the meaning of the invention, means connected, directly or indirectly with one or more intermediate elements. Two elements can be coupled mechanically, electrically or connected by a communication channel.

In the remainder of the description, the same references are used to designate the same elements. Furthermore, the different characteristics presented and/or claimed can be advantageously combined. Their presence in the description or in different dependent claims does not exclude this possibility.

As mentioned, for decades there has been a proliferation of footwear items and their use. Furthermore, footwear has remained a fashion object subject to trends, in particular temporal and geographical trends.

Faced with this proliferation of models and uses, manufacturers must try to keep themselves informed and regularly carry out market studies so as to be able to plan their production in terms of content, volumes and destination. Nevertheless, this research is laborious and requires the collection of a large volume of information and the results remain biased by the methodologies used.

To overcome this, the present invention proposes a solution based on the use of a connected sole and information processing allowing to extract use indicators that were previously inaccessible.

In particular, the present invention allows to determine the use of a footwear item by one or more users.

Thus, according to a first aspect, the invention relates to a system 1 for analyzing the use of footwear items 11. In particular, such a system is configured to determine one or more association indices between use parameters 101 and shoe parameters 201 relating to a footwear item 11.

For this purpose, and as illustrated in FIG. 1, a system 1 for analyzing the use of footwear items in accordance with the invention comprises a calculation computing device 30, and at least one connected sole 10 of a footwear item 11.

Furthermore, a system 1 for analyzing the use of footwear items in accordance with the invention may also include a presentation computing device 20 and a third-party computing device 40.

Thus, a system 1 in accordance with the invention comprises one or more calculation computing devices 30 configured to load posture or mobility parameter values 301 calculated from raw data generated by at least one connected sole 10 of a footwear item 11, load geographic parameter values 401, load shoe parameter values 201, calculate one or more use parameter values 101 and determine one or more association index values between the use parameters 101 and the shoe parameters 201. The loading of the parameter values can in particular correspond to the loading into memory of these data. A calculation computing device 30 may be configured to obtain these values and in certain cases it may be configured to calculate them for example from raw data.

A calculation computing device 30 according to the invention advantageously comprises a processing unit or a processor, for example in the form of a microcontroller cooperating with a data memory, possibly a program memory, said memories possibly being dissociated. Such a data memory can be configured to store a computer program whose program instructions, interpretable and executable by the processing unit, allow to automatically adapt a conventional computing device so that it becomes a calculation computing device 30 in accordance with the invention.

The data memory can be partially or entirely electrically erasable in order to be updated. Generally, a section of said data memory is not erasable by construction, or is protected against such erasure by a security mechanism. Such a memory section records in a durable manner, in particular the value of a unique identification datum characterizing a connected sole 10 with regard to other pair connected soles. The processing unit cooperates with said memories by means of an internal communication bus. Thus, the data from sensors positioned in said connected sole can be stored in such a data memory. Said data memory can further store personal data associated with the user of the connected sole. The calculation computing device 30 may be located in a cloud. Thus, the data from the sensor(s) positioned in the connected sole 10 can be related to the personal data of the user, through the value of the unique identification datum of the connected sole 10. The personal data associated with the user of the connected sole 10 can correspond to data accessible on request from a computing device configured to store such personal data. Advantageously, the personal data is entered by the user of the connected sole 10 via a dedicated application installed on a presentation computing device 20. Thus, the user can enter personal data such as his sex, his age, his weight, his height, his shoe size or more generally any morphometric or non-morphometric datum of interest in the context of the calculation of the values of the user's posture or mobility parameters. Thus, it is expected that the user can indicate, in the context of entering his personal information, one or more pathologies having an influence on his gait, or more generally any physical failure involving difficulty in moving. Such a pathology or physical failure can be selected via a list through the dedicated application or can be entered in a dedicated field. Such a pathology or such a physical failure may consist advantageously but in a non-limiting manner of articular problems of one or more limbs of the user, a hallux valgus, a hallux rigidus, a claw toe ("hammer toe"), a bunionette, Morton's syndrome, 2nd ray pain syndrome, intermetatarsal bursitis, sesamoidopathies, tendinopathies or any physical injury affecting the user's gait. In addition, through the application accessible via the presentation device, the user can also enter data relating to his daily activities, for example through a daily questionnaire, and can thus indicate a period (that is to say an interval corresponding to a time slot) of daily sleep. Such a questionnaire can also allow the user to enter data relating to a given period of daily activity and in particular the type of activity practiced whether it is of a sporting nature or not. This advantageously allows to determine with more precision, from the personal data entered by the user, a use parameter value according to the different daily periods.

Such a calculation computing device 30 also comprises communication means configured to communicate through a long-range communication network R1 of the Internet, LoRa or Sigfox type or any other equivalent communication network. Advantageously, a calculation computing device 30 according to the invention can correspond to a computing server or else to an electronic unit of a connected sole 10. Of course, a calculation computing device 30 according to the invention cannot be limited to a computing server and may also correspond to a computer-type computing machine further comprising a man-machine interface, that is to say any element allowing a human being to communicate with a particular computer and without this list being exhaustive, a keyboard and means allowing, in response to commands entered on the keyboard, to perform displays and optionally to select, using a mouse or a touchpad, elements displayed on a screen. Another exemplary embodiment is a touch screen allowing to select directly on the screen the elements touched by the finger or an object and optionally with the possibility of displaying a virtual keyboard.

A calculation computing device 30 in accordance with the invention can advantageously communicate with computing devices, such as a presentation computing device 20 or else with a connected sole 10 equipping a footwear item 11.

Indeed, one of the advantages of the invention is to be able to rely on raw data generated by one or more connected soles 10 in order to be able to determine the use made by the user of the footwear item 11 to which the sole is connected 10.

For this purpose, a footwear item 11 corresponds to a shoe intended to be worn by a user. Generally, the user will wear two footwear items 11, one on each foot. The footwear items 11 will be equipped with one, preferably two connected soles 10 (that is to say one connected sole 10 per footwear item).

A connected sole 10 is configured to generate raw data from which it is possible to calculate mobility or posture parameter values 301. Such raw data can be sent directly to the calculation computing device 30 which will then be configured to calculate the mobility or posture parameter values 301 from the raw data received and to store them in its data memory. Provision is also made for the raw data generated by a connected sole 10 to be transmitted to a third-party computing device which will then be configured to calculate the mobility or posture parameter values 301 from the raw data received. The mobility or posture parameter values 301 can thus be loaded either directly from the data memory of the calculation computing device 30 or from the third-party computing device. In a particular embodiment, a connected sole 10 may comprise hardware and software resources configured to calculate mobility or posture parameter values 301.

The mobility or posture parameters 301 can correspond to biomechanical parameters. Thus, the mobility or posture parameters 301 can be selected, for example, from: pronation/supination values, impact force values, pace length values, contact time values, acceleration, angular speed values, sole orientation values, propulsion speed, fatigue rate, Fick angle, a propulsion direction and a deceleration direction. Such parameters may also correspond to the pace length, the contact time, time of flight, lameness, propulsion force, balance and several other parameters relating to the user and describing his gait, postures and his movements.

Advantageously, the most relevant mobility or posture parameters 301 in the context of the present invention are: the parameters related to the health of the person such as the impact force parameter on contact with the ground (in particular if it shows a high value), pronation and/or supination parameters (in particular if they show a high value), and/or lameness. Furthermore, the shoe wear parameter is also very relevant, in particular because it can create injuries.

Even more preferably, the mobility or posture parameters 301 include at least: the impact force parameter, the pronation parameter and/or the supination parameter.

Figure 2:
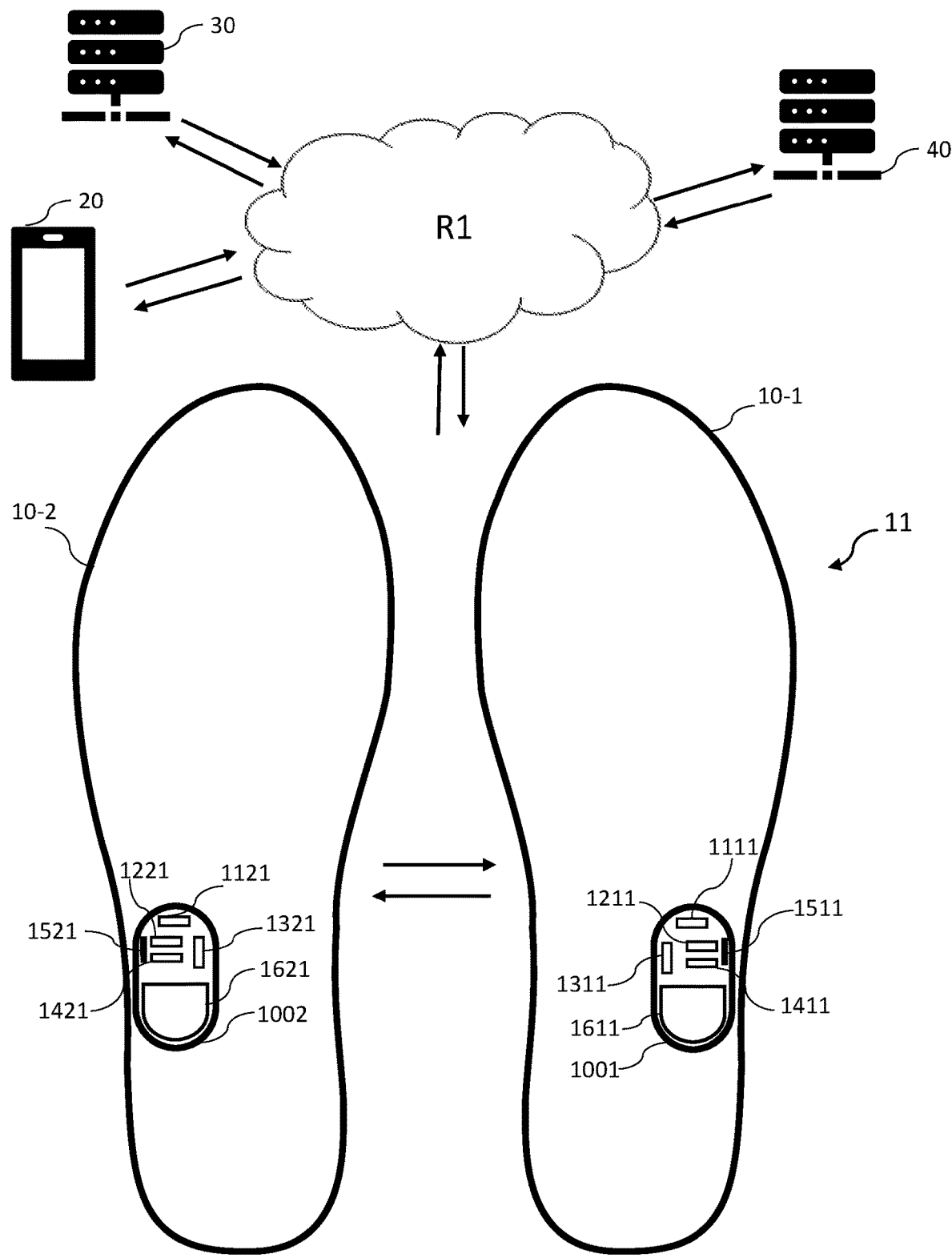
FIG. 2 shows a system for analyzing the use of footwear items according to the invention detailing an electronic unit of a connected sole.

As illustrated in FIG. 2, it will be assumed that a footwear item 11 comprises a pair of shoes equipped with a pair of connected soles. In each of said shoes, an electronic unit 1001, 1002 is arranged in a sole of each of said shoes, thus corresponding to a connected sole according to the invention referenced 10-1, 10-2 in connection with FIG. 2.

The connected soles according to the invention can for example correspond to outer soles or to inner soles of a footwear item. These soles can be removable or be permanently integrated into the sole assembly of the footwear item.

Conventionally, the connected soles 10-1, 10-2 each include an electronic unit 1001, 1002. As shown in FIG. 2, the electronic unit 1001, 1002 is preferably positioned at a middle portion of the sole.

An electronic unit 1001, 1002 advantageously weighs only a few grams and has a reduced size adapted for a sole of a shoe, this electronic unit 1001, 1002 is housed in a space-saving manner in any inner and/or outer sole. This low volume limits the impact on user comfort and has the advantage of optimizing production costs by making it less expensive and simpler to integrate this technology into the sole during the industrial process.

The choice of material for the electronic unit 1001, 1002 is made in such a way as to ensure its solidity as well as the possibility of inserting it into a sole. Indeed, it is necessary to be able to manufacture a product which can, on the one hand, withstand the weight of a person and, on the other hand, be easily inserted into a sole or a shoe. Combining miniaturization and resistance of the unit is a real challenge: many prototypes had to be made before determining the material that would allow such a unit to be inserted into a sole, without altering the comfort of the latter.

Such an electronic unit 1001, 1002 includes an inertial platform 1111, 1121 configured to generate a set of data on the gait of a user wearing a footwear item 11 including at least one connected sole 10. In particular, the inertial platform 1111, 1121 is configured to generate a set of data on a movement of the foot of a user equipped with the at least one connected sole 10.

While a user is walking, the inertial platform 1111, 1121 acquires signals representative of a movement parameter (acceleration and/or speed, for example angular speed) of the foot along the axes X, Y, Z. Furthermore, these data can then be processed to generate at least one acceleration signal.

The electronic unit 1001, 1002 can also include one or more magnetometers so as to acquire three additional raw signals corresponding to the magnetic field values in three dimensions.

Each electronic unit 1001, 1002 can also include other sensors, in particular an inclinometer, a barometer, a temperature sensor, a humidity sensor and an altimeter to benefit from increased precision. Furthermore, the electronic unit can be coupled to other sensors, for example distributed in the sole, such as pressure sensors or force sensors. In particular, the pressure and/or force sensors can include electrodes and be made of piezoelectric materials.

The inertial platform is for example made up of at least one accelerometer and one gyroscope. Preferably, it includes several accelerometers and gyroscopes. More preferably, the inertial platform 1111, 1121 includes at least one accelerometer and at least one gyroscope, and can be supplemented by other sensors, in particular a magnetometer, a barometer and an altimeter.

Furthermore, advantageously, the data generated by the electronic units 1001, 1002 are encrypted. In this case, advantageously, only the computing device intended to receive said generated data is configured to decrypt them.

In particular, the data generated by the electronic units 1001, 1002 are encrypted using public keys each associated with one of the electronic units and the calculation computing device 30 can have the private keys necessary for decrypting the data generated.

Furthermore, the electronic unit 1001, 1002 may include a data processing module 1211, 1221 configured to transform all the data generated using predefined algorithms. Thus, the electronic units 1001, 1002 can be configured to process the signals generated by the inertial platform so as to facilitate subsequent processing by a computing device. The data received via the sensors located in the inner and/or outer soles are processed according to one or more algorithms in each of the electronic units. The processing module is advantageously configured to carry out a pre-processing of the data generated and optionally to carry out a sufficient processing to generate information on the posture or the gait of the user, information that the electronic unit transmits to a computing device, in real time or offline with the raw data.

The electronic units 1001, 1002 can also be configured as a slave unit, which receives the data generated by the sensors located in its sole/shoe and transmits them to the master unit, called the main unit, which receives the data from the master unit, processes them by comparing them with its own data and generates information on the posture of the user in general and of his feet in particular, information that the master unit transmits to a computing device in real time or offline.

The processing module 1211, 1221 allows to analyze in 3D the posture, the movements, the locomotion, the balance and the environment of the user, and more generally all that will be qualified as being his walk, from the data collected by the inertial platform and any additional sensors placed in the sole.

The processing module 1211, 1221 can be used to generate biomechanical gait parameters. Advantageously, the processing module 1211, 1221 is configured to transform the set of data into at least one mobility or posture parameter 301 such as those mentioned above.

Furthermore, the transformation by the processing module 1211, 1221 can advantageously comprise the segmentation of the data into a plurality of phases. Preferably, the data processing module 1211, 1221 is able to segment a pace into at least four phases such as: the impact phase (corresponds to the precise moment of contact of the foot with the ground), the bearing phase (takes place from the impact phase until the heel lifts off the ground), the propulsion phase (begins when the heel leaves the ground and ends when the first toe leaves the ground) and the flight phase (starts when the first toe leaves the ground and ends when the heel touches the ground).

More specifically, the division or segmentation of the pace can allow to identify the main bearing areas for the user. Thus, it is possible to measure the shape of the pace during walking or any other activity of the user in order to determine the possible malformations of the feet and postures of the user.

The information generated will then be transmitted to the second electronic unit 1002, or more generally to the master unit or main unit by emitting signals which may, by way of non-limiting example, be of the Bluetooth type.

The electronic unit 1001, 1002 can advantageously be formed by encapsulating its components. For example, the encapsulation can be in the form of a conformal coating or a resin (e.g. silicone, epoxy, polyurethane). The encapsulation of all the components (e.g. inertial platform, processing module, . . . ) provides good insulation and thus combines good electrical properties with excellent mechanical protection.

When an electronic unit is not able to communicate in real time with the other unit and/or with the computing device, it stores the information collected and transmits it offline when the exchange is again possible. This offline transmission of the data collected is made possible thanks to the storage capacity with which each of the electronic units is equipped.

Thus, the electronic unit includes a data storage module 1311, 1321, configured to memorize at least part of the transformed data and/or the data generated by the processing module. Such a data storage module 1311, 1312 can advantageously have a memory capacity of less than 512 kB, preferably less than 128 kB, more preferably less than 32 kB and even more preferably less than 16 kB. In particular, the storage module can correspond to the memory available on a CPU.

Furthermore, the electronic unit 1001, 1002 includes first communication means. Thus, in particular, each of the electronic units is designed so as to be able to communicate independently with the other and/or directly with a computing device or else with a communicating electronic device in order to be able to exchange its own information on the posture/the movement/the activity of its foot, from which it received the data via the various sensors of the inner and/or outer sole of the shoe thus equipped.

Preferably, the electronic unit 1001, 1002 includes first communication means 1411, 1421 configured so that the electronic unit 1001, 1002 of at least one of the soles is able to transmit at least part of the raw data, in real time or offline, to a calculation computing device 30 or to a third-party computing device 40 or else to a presentation computing device 20. As presented, these data are preferably data called raw data, that is to say data as generated by the inertial platform (preferably 9 axes and at least at 200 Hz), but can also be preprocessed data or posture or mobility parameter values 301.

Advantageously, each electronic unit 1001, 1002 includes second communication means configured so that the electronic unit 1001 of a connected sole is able to communicate with the electronic unit 1002 of a second connected sole. Thus the electronic units 1001, 1002 will be able to exchange information in real time. Indeed, the generation of data by the inertial platforms must preferably be synchronized and this advantageously involves communication between the two electronic units 1001, 1002. More preferably, the electronic units 1001, 1002 are configured so as to be able to punctually check their synchronization.

In particular, the two electronic units 1001, 1002 are configured to communicate with each other and to initiate the generation of data on the movement of a user's foot only after receiving a message from the other electronic unit.

The first and second communication means are capable of receiving and transmitting the data over at least one communication network R1. Preferably the communication is operated via a wireless protocol such as wifi, 3G, 4G, and/or Bluetooth. Preferably the communication protocol is a BLE or ANT+ protocol. These communication protocols allow low energy consumption.

Advantageously, each of the units 1001, 1002 is designed so as to be able to communicate with the second unit, for example by short wave or high frequency signals of the Bluetooth Low Energy or ANT+ type.

Thus, in particular, each of the units, whether master or slave unit, is designed so as to be able to communicate independently with the other and/or directly with a computing device in order to be able to exchange its own information on the posture/the movement/the activity of its foot, from which it has received data via the various sensors of his inner and/or outer connected sole of a footwear item.

Advantageously, due to its confinement inside a unit placed under the body of a person, the antenna 1511, 1521 should preferably be disposed inside the unit on the side facing the outside of the sole. This positioning of the antenna is preferable insofar as laboratory tests have established that the signal emitted from a sole or shoe is 70% absorbed by the human body. This antenna must therefore be positioned on the periphery of the foot and oriented in such a way as to always be able to transmit the signal to the unit of the second sole. Preferably, the antenna can be an antenna printed on an electronic card. Alternatively, the antenna can be printed on an inner face of the unit and connected to the electronic card by wiring. The antenna can preferably be positioned on a low part with respect to the electronic card. Thus, the electronic card makes contact with the antenna.

Furthermore, the electronic unit 1001, 1002 includes an energy source 1611, 1621. The energy source is preferably of the battery type, which is rechargeable or not. Preferably the power source is a rechargeable battery. Furthermore, it can be associated with a system for charging by movement or by external energy. The system for charging by external energy can in particular be a system for charging by wired connection, a system for charging by induction or else a photovoltaic system.

The electronic unit 1001, 1002 can include a power source 160 of the rechargeable battery type, the recharging of which can be carried out using different technologies:
- by charger, with a connector flush with the sole;
- with a mechanical recharging device integrated into the sole, such as for example a piezoelectric device capable of supplying electrical energy from walking;
- with a contactless device, for example by induction; or
- with a photovoltaic device.

Furthermore, the electronic unit according to the invention may include a wired connection means, preferably protected by a removable tab. Such a tab can preferably be made of a polymer of the elastomer or polyurethane type. This wired connection means can for example be a USB or firewire port. Advantageously, the USB port is also resistant to water or humidity. This wired connection means can be used as mentioned above to recharge the battery but also to exchange data and for example update the firmware of the electronic card carrying the various components of the electronic unit.

These various components of the electronic unit are preferably arranged on an electronic card (or printed circuit). Furthermore, the various means and modules of the electronic unit 1001, 1002 are represented separately in FIG. 2, but the invention may provide for various types of arrangement such as for example a single module combining all the functions described here. Likewise, these means can be divided into several electronic cards or even combined on a single electronic card.

Furthermore, a system 1 in accordance with the invention comprises a presentation computing device 20 that can be configured to receive raw or preprocessed data, generated by a connected sole 10 or more particularly by an electronic unit 1001, 1002. The presentation computing device 20 is generally a tablet, a smartphone. It can be configured to transfer its data to a remote calculation computing device. It is then possible, for example, to access this remote computing device via a web interface.

Advantageously, a dedicated application is installed on the presentation computing device 20 in order to process the information transmitted by the units and allow the user to interact with the computing device in charge of processing the raw data generated by the connected sole 10. In particular, the user will be able to consult all the parameter values generated by the connected sole or else by the calculation computing device 30. Thus, a connected sole 10 can be associated, preferably coupled directly or indirectly, to a computing device presentation 20.

In particular, a system 1 according to the invention comprises a calculation computing device 30 configured to determine the use of a footwear item by one or more users.

A calculation computing device 30 according to the invention can be configured to receive posture or mobility parameter values 301 calculated from raw data generated by at least one connected sole 10 of a footwear item 11. The posture or mobility parameter values 301 are calculated from the raw or preprocessed data generated by each connected sole 10. Said posture or mobility values 301 can be calculated directly by the processing module 1211, 1221 of a connected sole 10 or else by a calculation computing device 30 upon reception of the data generated by the connected sole 10. Alternatively, the data generated by the connected sole 10 are sent to a third-party computing device 40 configured to calculate said posture or mobility values 301.

Furthermore, in an embodiment not shown, the calculation computing device 30 corresponds to the electronic unit of the connected sole 10 and it is not necessary for the connected sole 10 to transmit raw data, preprocessed data or posture or mobility parameter values 301.

For example, the calculation computing device 30 may correspond to a computing server accessible remotely, a computer, a connected object such as a telephone or a tablet or it may correspond to the electronic unit of a connected sole.

The calculation computing device 30 according to the invention can be configured to receive geographic parameter values 401. The geographic parameter values 401 can be transmitted by a presentation computing device 20 coupled to at least one connected sole 10. Indeed, the user can, through a dedicated application, or else via a Bluetooth type communication retrieve the data generated by the connected sole. Said data generated by the connected sole can thus be sent to the presentation computing device 20 to which said connected sole is coupled. The data generated by the connected sole can thus be compiled with geographic positioning data from the presentation computing device 20. Indeed, provision is made for the presentation computing device 20 to comprise a geolocation and satellite navigation module allowing to determine the geographic positioning of said computer presentation device 20, at a given time. Furthermore, provision is also made for the connected sole 10 to be able to include a geolocation and satellite navigation module and thus transmit its geographical position directly to a calculation computing device 30. Such geographic parameter values 401 can correspond to any coordinate format known and used by satellite positioning systems, such as the American GPS (for "global positioning system") system or else the European Galileo system. The invention cannot be limited to the reception of geographical parameter values, provision is made for the presentation computing device 20 to be able to communicate other parameters such as a timestamp of the data transmitted by the connected sole 10 when the user is wearing a footwear item 11 equipped with connected soles 10, such a timestamp allowing to define time periods during which the footwear item 11 is used. Furthermore, provision is made for the presentation computing device 20 to be able to transmit data relating to the external environment, such as meteorological data which may comprise the external temperature, the humidity level, etc., in connection with the geographical parameter values.

The calculation computing device 30 according to the invention is configured to obtain or load shoe parameter values 201. The shoe parameters aim at describing the characteristics of the footwear item used during operation of the connected sole. These shoe parameters may concern both the technical characteristics of the shoes and the aesthetic or behavioral characteristics. This may include the shape, the properties of the materials used, possibly the mechanical characteristics, in particular of the sole. The shoe parameter values 201 can advantageously be stored in a database of the calculation computing device 30 or else on a third-party computing device 40. Indeed, it is provided that each connected sole 10 can be associated with a specific footwear item 11. By way of non-limiting example, the third-party computing device 40 can comprise a database, in particular that of a manufacturer or else a retailer, indicating for each connected sole 10 to which model of footwear item said connected sole is associated. It is thus possible to associate shoe parameter values with a connected sole 10 and by extension to associate the data generated by said connected sole with a user equipped with a particular model of footwear item.

The shoe parameter values may include values of structural parameters, geometric parameters and/or aesthetic parameters of the footwear item 11 including the at least one connected sole 10.

In particular, the shoe parameter values 201 can include structural parameter values indicating the different elements constituting a model of predetermined footwear item 11. The shoe parameter values 201 can thus indicate the presence of a stiffener, a hard toe, a sole, a shank, a mounting insole, a sock liner, a stem. More particularly, the shoe parameter values 201 can describe the shape of each of the elements constituting the footwear item 11 and their arrangement. The shoe parameter values 201 may further include geometric parameter values. Said geometric parameter values can indicate the dimensions relating to each of the structural elements of the footwear item 11. Finally, the shoe parameter values 201 can also include aesthetic parameter values indicating for example for each structural element a color, a type of material, a particular aesthetic pattern.

For example, shoe parameters may include technical or physical parameters such as, by way of non-limiting examples:

a value associated with the cushioning,
a value associated with adhesion,
a value associated with the "drop" of the sole of the footwear item 11, that is to say the difference in height between the heel and the front of the foot or in other words the difference between the thickness of the sole at the back and at the front of the footwear item 11, a high "drop" resulting in increased use of the heel in the attack phase of the foot during a stride and therefore puts more strain on the athlete's knees,
a value associated with flexibility,
a value associated with robustness,
a value associated with the presence of a reinforcement, and/or
a category value describing in particular whether the footwear item 11 belongs to a stride of the universal type, an over-pronator or a supinator stride.

Shoe parameters may also concern:
the type of sport or activity to which the footwear item 11 corresponds,
the brand associated with the footwear item 11, and/or
an identifier of the connected sole 10 associated with the footwear item 11.

A calculation computing device 30 according to the invention is further configured to calculate, for each connected sole 10, one or more use parameter values 101 from the posture or mobility parameter values 301. For this purpose, the calculation computing device 30 advantageously comprises, in a dedicated data memory, a use repository. The use repository can include reference posture or mobility values with which a predetermined type of use is associated. By way of non-limiting examples, the determination of a use can be associated with a pattern of specific reference posture or mobility values. The determination of a use may also be subject to whether or not a predetermined threshold is exceeded. The person skilled in the art will appreciate that the possibilities for determining a use according to the posture or mobility parameters are very numerous and that it will be possible to configure the calculation computing device 30 to calculate one or more use parameter values 101 according to posture or mobility parameters 301 deemed relevant for a given use.

By way of non-limiting examples, a use parameter value may indicate a sporting, urban, recreational use of a footwear item 11. For this purpose, the calculation computing device 30 can be configured to identify in the posture or mobility parameter values 301 previously loaded, values describing an impact force, a pace length, an acceleration, a speed of propulsion and a time of flight. In particular, the calculation computing device 30 may be configured to compare values describing an impact force, a pace length, an acceleration, a propulsion speed, and a time of flight to a plurality of reference value patterns for these posture and mobility parameters taken alone or in combination. The person skilled in the art will understand that in the context of sports practice one or more parameters may be taken into account to identify a use of a footwear item. In particular, a sports practice of the running type could, for example, be characterized by values describing an acceleration, a particular time of flight or else a pace length or a running speed or else a combination of these parameters. It may also be interesting to identify which footwear item 11 is used for a given use by a user category. For this purpose, the posture or mobility parameter values 301 taken into account can include pronation and/or supination values. In the context of problems more related to the field of health, affecting for example the gait of a user, other posture or mobility parameters could be taken into account to identify which footwear item 11 is used, for a given use, by a user category. In particular, the posture or mobility parameters, affecting the user's gait, which can be analyzed are the presence of lameness, a fatigue rate, orientation values of the sole, balance. Thus, it will be possible to determine on the one hand a particular use of a footwear item in the context of a sports practice for example, for a given user category.

The calculation computing device 30 according to the invention is further configured to determine, for each connected sole 10, an association index value between the use parameter values 101 and the shoe parameter values 201. This index value can in particular allow to determine whether the footwear items are used as planned during their design and in connection with their mechanical properties. Unanticipated uses may correspond to trends on the one hand but also to risks on the other hand. The association index value can be considered as the result of a correspondence analysis between the use parameter values 101 and the shoe parameter values 201. The system according to the invention could therefore in certain aspects be considered as a correspondence engine or even a recommendation system which establishes correspondence between activities and the initial destination of the footwear items, knowing that it can advantageously integrate many other parameters such as the terrain, the environment, the geography, the weather, . . .

For this purpose, the calculation computing device 30 advantageously comprises, in a dedicated data memory, an association repository. The association repository includes for shoe parameter values 201, a reference use parameter value. By way of non-limiting example, it is provided that each footwear item 11 can be described through shoe parameter values 201. One or more of the shoe parameter values 201 can advantageously be associated with a use parameter value 101. The person skilled in the art will appreciate that depending on the recommended use, for a sporting activity for example, a footwear item has shoe parameter values 201 specific to said recommended use. Thus, the calculation computing device 30 is advantageously configured to determine an association index value which can, for example, be in the form of a value comprised between 0 and 1 characterizing a concordance between the use value(s) of the use parameter 101 calculated from the posture or mobility parameter values 301 for the footwear item 11 whose shoe parameter values 201 have been loaded.

Indeed, it is possible that the user uses a footwear item 11 equipped with a connected sole in accordance with the invention for a rather sporting use or then for use in everyday life and therefore rather associated with a less dynamic gait. Thus, the calculation computing device 30 will be able to determine, for a series of posture or mobility parameter values 301 calculated from raw data generated by at least one connected sole 10 over a given time interval, a use parameter value 101. By way of non-limiting example, an association index value close to 1 will mean that the use parameter value(s) 101 calculated correspond to the reference use value associated with the shoe parameter values 201 comprised in the association repository for the footwear item 11. On the contrary, an association index value close to 0 will mean that the calculated use parameter value(s) 101 do not correspond to the reference use value associated with the shoe parameter values 201 comprised in the association repository for the footwear item 11.

The calculation computing device 30 in accordance with the invention can further be configured to identify a conventional and/or unconventional use, by a user, of a footwear item 11 including a connected sole 10. Such an identification can correspond to a comparison operation of the use parameter value(s) 101 calculated with a reference use value comprised in the association repository for the footwear item 11 comprising the connected sole 10 whose generated data allowed to calculate the use parameter value(s) 101. In the case where the reference use value is equal to the calculated use parameter value, then the use of the footwear item 11 including the connected sole 10 is considered as conventional. Conversely, if the reference use value is not equal to the calculated use parameter value, then the use of the footwear item 11 including the connected sole 10 is considered to be unconventional.

The calculation computing device 30 according to the invention can also be configured to calculate an overall association index value from all the association index values previously determined for each connected sole 10. Indeed, it may be advantageous to determine, for a model of footwear item 11, what use is made by a set of users of said model of footwear item 11. Thus, a global association index value can correspond to an average calculated from a plurality of association index values previously calculated from the data generated by each connected sole equipping a model of footwear item used by a plurality of people.

In order to determine a trend of use of a predetermined model of footwear item 11, a calculation computing device 30 in accordance with the invention can be configured to calculate an overall association index value by taking into account only the data generated by one or more connected soles 10 of a predetermined geographical area. Such a geographical area may correspond to a set of geographical coordinates, for example defined by longitude, latitude and/or altitude relative to the mean sea level, describing the perimeter of a surface of a territory, such as by way of non-limiting example the geographical coordinates describing a country. As described above, a calculation computing device 30 according to the invention is configured to load geographic parameter values 401, said geographic parameter values corresponding to a location of the at least one connected sole 10. Thus, the data generated by each connected sole 10 are associated with one or more geographical coordinates, and therefore, consequently, the parameter values calculated from said data are also associated with the connected sole 10. The calculation computing device 30 can be configured to filter the data produced by one or more connected soles 10 taking into account only the connected soles 10 whose geographic parameter values 401 indicate a location of the corresponding connected sole in a determined geographical area. Such a trend of use could thus be compared with a monitoring of trends, in particular concerning the number of sales associated with a model of footwear item, observed in a plurality of geographical areas, on social network platforms, in particular with particular profiles such as influencer profiles, or digital advertising media.

In order to facilitate the identification, by the calculation computing device 30 in accordance with the invention, of the data generated by a connected sole 10, in particular the posture or mobility parameter values 301, the values of geographic parameter values 401, shoe parameter values 201, use parameter values 101 and association index values, all the data and/or values loaded and calculated can be associated with a unique identifier of the corresponding connected sole 10.

To improve and better understand the use that is made of a model of footwear item 11, provision is made for the calculation computing device 30 according to the invention to be able to be configured to identify a plurality of connected third-party soles 10' each being associated with another footwear item 11' having shoe parameter values 201' substantially identical to the shoe parameter values 201, that is to say with another model of footwear item than that related to the footwear item 11. Indeed, it is particularly advantageous to be able to identify whether the conventional or non-conventional use of a footwear item 11 is specific to a certain model or whether such conventional or non-conventional use is observable on other models of footwear items 11'. The calculation computing device 30 can then be configured to identify in a database referencing a multitude of footwear items, a shoe parameter value describing a category associated with a footwear item and corresponding to the category of the footwear item 11. Such identification can also consist in a comparison of all the shoe parameter values 201 of the footwear item 11 with the shoe parameter values of the footwear items referenced in the database, in order to determine another footwear item 11' having shoe parameter values 201' substantially identical to the shoe parameter values 201.

To improve and better understand the use that is made of a model of footwear item 11, provision is made for the calculation computing device 30 according to the invention to be able to be configured to identify a plurality of connected third-party soles 10' each being associated with another footwear item 11' having posture or mobility parameter values 301' substantially identical to the posture or mobility values 301, that is to say with another model of footwear item than that related to the footwear item 11. Indeed, it is particularly advantageous to be able to identify whether the conventional or non-conventional use of a footwear item 11 is specific to a certain model or whether such conventional or non-conventional use is observable on other models of footwear items 11'. The calculation computing device 30 can then be configured to identify in a database referencing a multitude of footwear items, one or more posture or mobility parameter values describing a use of a footwear item by a user of the third-party connected sole 10'. Such an identification may consist of a comparison of all the posture or mobility parameter values 301 of the footwear item 11 with the posture or mobility parameter values of the footwear items referenced in the database, in order to determine another footwear item 11' having posture or mobility parameter values 301' substantially identical to the posture or mobility parameter values 301.

It is thus possible to identify other footwear items 11' by means of posture or mobility parameter values 301' which are substantially identical and/or shoe parameter values 201' which are substantially identical to those of the footwear item 11. For this purpose, the calculation computing device 30 can store such a database referencing a multitude of footwear items, preferably each of the referenced footwear items comprises a third-party connected sole 10'. Alternatively, such a database referencing a multitude of footwear items can be stored in a third-party computing device 40.

To improve and better understand the use that is made of a model of footwear item 11, provision is made for the calculation computing device 30 according to the invention to be able to be configured to identify a plurality of connected third-party soles 10' each being associated with another footwear item 11' having geographical parameter values 401' substantially identical to the geographical parameter values 401, that is to say with another model of footwear item than that related to the footwear item 11. Indeed, it is particularly advantageous to be able to identify whether or not the geographical use of a footwear item 11 is specific to a certain model or whether such geographical use is observable on other models of footwear items 11'. The calculation computing device 30 can then be configured to identify in a database referencing a multitude of footwear items, a geographic parameter value describing a category associated with a footwear item and corresponding to the category of the footwear item 11. Such an identification can also consist of a comparison of all the geographical parameter values of the footwear item 11 with the geographical parameter values of the footwear items referenced in the database, in order to determine another footwear item 11' having geographical parameter values substantially identical to the geographical parameter values 401.

Furthermore, the calculation computing device 30 according to the invention may be configured to use data originating from other devices such as cardiac data, diary data, movement data originating for example from connected watches or other computing devices.

In order to provide a footwear item adapted to the use of a user, the calculation computing device 30 according to the invention can further be configured to generate design parameters of footwear items 11 on the basis of the determined association index values between the use parameter values 101 and the shoe parameter values 201. Indeed, the calculation computing device can in particular be configured to generate a personalized digital model from the shoe parameter values of the footwear item associated with the connected sole. The shoe parameter values of said footwear item can thus be optimized, that is to say personalized by taking into account the use made of them by the user. It is thus possible to determine new shoe parameter values in line with the use of the user, such as, by way of non-limiting examples, shoe parameter values related to a thickness of the midsole, increased outsole abrasion resistance, stiffness, insulation, greater midsole cushioning properties. In this way, the midsole, and more generally the footwear item, can be adapted to the use of the user in an optimal manner.

In order to allow the manufacture of a footwear item adapted to the use of a user, the calculation computing device 30 can also be configured to generate production parameters relating to the manufacture of footwear items 11 on the basis of the determined association index values between the use parameter values 101 and the shoe parameter values 201. Such production parameters can comprise the materials used, their shape and their dimensions, but also the design of the footwear item (for example colors, logos, applications, etc.) or its functional properties (for example impermeability, cushioning, etc.) and can then be updated according to the use parameter values 101 obtained.

In order to allow the routing of footwear items adapted to the use of a user, the calculation computing device 30 can also be configured to generate values of logistics parameters relating to the manufacture and distribution of footwear items 11 on the basis of geographic parameter values 401, determined association index values between the use parameter values 101 and the shoe parameter values 201. More particularly, it may be advantageous to determine, from the geographical parameter values, one or more points of sale within a radius comprised between 1 kilometer and 20 kilometers in order to establish a shipment route and to determine an adapted transport means.

According to another aspect, the invention relates to a method 500 for analyzing the use of footwear items 11 to determine an association index between use parameters 101 and shoe parameters 201. Such a method is implemented by a calculation computing device 30 within a system 1 in accordance with the invention.

Figure 3:
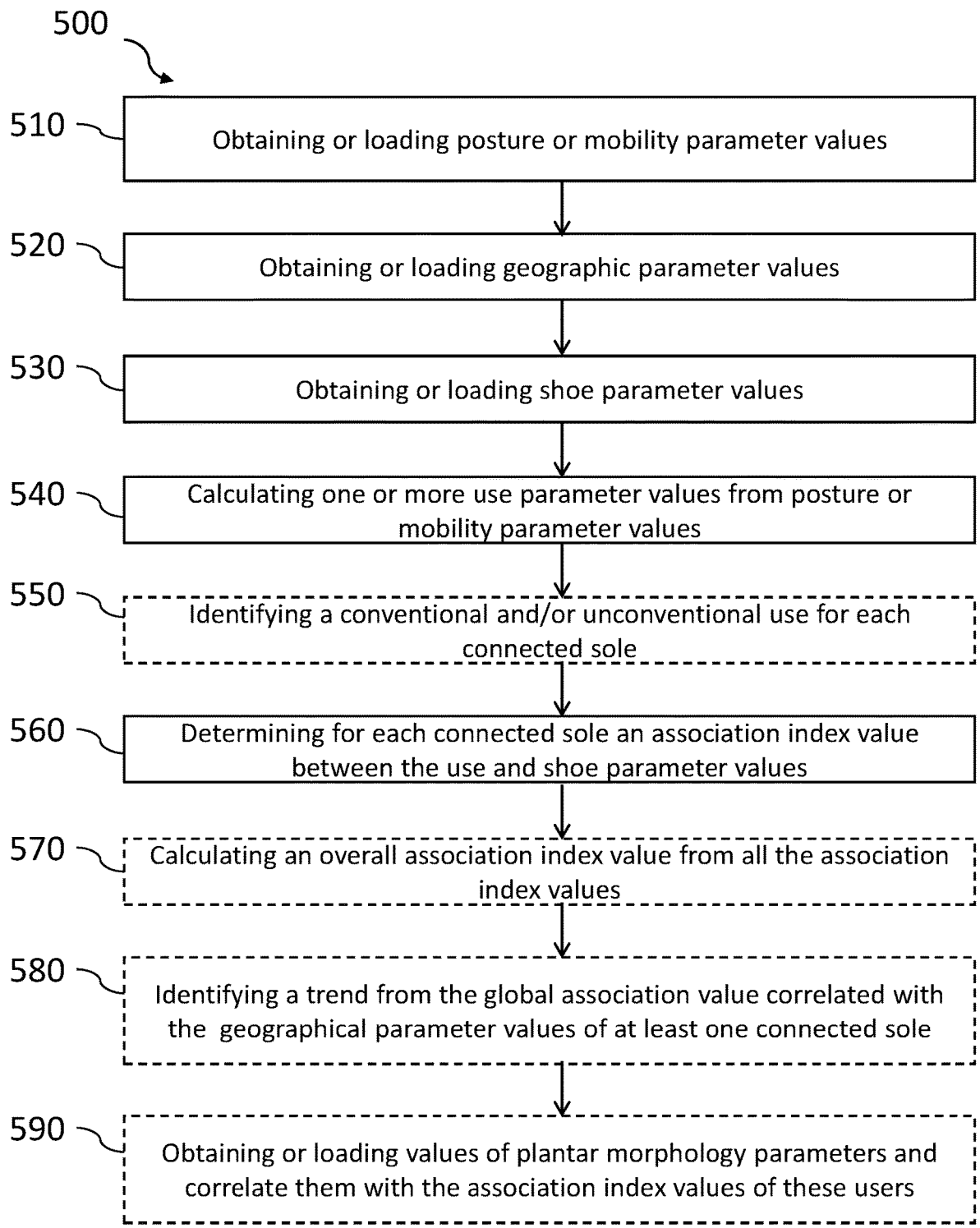
FIG. 3 shows a method for analyzing the use footwear items according to one embodiment of the invention.

As illustrated in connection with FIG. 3, an analysis method 500 according to the invention comprises a step of loading 510 the posture or mobility parameter values 301, a step of loading 520 the geographical parameter values 401, a step 530 of loading shoe parameter values 201, a step 540 of calculating, for each connected sole 10, one or more use parameter values 101, a step 560 of determining, for each connected sole 10, of an association index value.

A loading step 510, of a method in accordance with the invention, consists in retrieving the posture or mobility parameter values 301 calculated from raw data generated by at least one connected sole 10 of a footwear item 11. The posture or mobility parameter values 301 can be transmitted either by the connected sole 10 directly to the calculation computing device 30, or by a presentation computing device 20 associated or coupled to the connected sole 10 or else by a third-party computing device 40 configured to store the raw data generated by the at least one connected sole 10 and calculate associated posture or mobility parameter values 301.

A loading step 520, of a method in accordance with the invention, consists in retrieving the geographical parameter values, from the connected sole 10, or from a third-party computing device 40, or else from the presentation computing device 20 coupled or associated with said connected sole. The geographical parameter values thus allow to locate the connected sole 10 and consequently the user.

A loading step 530, of a method in accordance with the invention, consists in retrieving the shoe parameter values 201 including values of structural parameters, geometric parameters and/or aesthetic parameters of the footwear item 11 including the at least one connected sole 10. Preferably, the shoe parameter values 201 are stored in a dedicated database, memorized in a data memory of a third-party computing device 40 accessible through an appropriate communication network or else directly in a data memory of the calculation computing device 30.

A calculation step 540, of a method in accordance with the invention, of one or more use parameter values 101, for each connected sole 10, is then implemented by the calculation computing device 30, from previously loaded posture or mobility parameter values 301.

A determination step 560, of a method according to the invention, for each connected sole 10, of an association index value between the use parameter values 101 and the shoe parameter values 201 is then implemented by the calculation computing device 30.

These calculation 540 and/or determination 560 steps could implement a learning model configured to refine the results according to the values that led to the selection of a use parameter value 101 or of an association index value. Learning can be a supervised or unsupervised learning. The method or system according to the invention is able to implement algorithms based on supervised or unsupervised learning methods. Thus, advantageously, the system or method for analyzing the use of footwear items according to the invention is configured to train and implement one or more algorithms. These algorithms may have been built from different learning models, in particular supervised or unsupervised partitioning. The algorithm can be derived from the use of a supervised statistical learning model selected for example from kernel methods (e.g. Support Vector Machines SVM, Kernel Ridge Regression) described for example in Burges, 1998 (Data Mining and Knowledge Discovery. A Tutorial on Support Vector Machines for Pattern Recognition), ensemble methods (e.g. decision trees) described for example in Brieman, 2001 (Machine Learning. Random Forests), k-means partitioning, decision trees, logical regression or neural networks described for example in Rosenblatt, 1958 (The perceptron: a probabilistic model for information storage and organization in the brain) or else deep learning (Kernel Methods for Pattern Analysis Hardcover—Illustrated, Cambridge University Press, 2004; Machine learning techniques on ultra-low energy microcontrollers: TinyML, Machine Learning with TensorFlow Lite on Arduino and Ultra-Low-Power Microcontrollers, O'Reilly, 2020; Dimensionality reduction techniques for hyper-dimensional data, Topological Methods in Data Analysis and Visualization V: Theory, Algorithms, and Applications Mathematics and Visualization, Springer Verlag, 2020.)

As part of a determination step, for each connected sole, of an association index value between the use and shoe parameter values, a method according to the invention may include the generation of an alert to the user of the connected sole. Such an alert may be in the form of digital media informing, for example, of a mismatch between the use made of the shoe and its original destination. A personalized digital media encodes, for example, one or more information in a format selected from the format: Text, images, video, sounds and their combinations.

For example, when the user uses footwear items for rock climbing or in the rain while the footwear item has a grip value adapted for such use, the method according to the invention may include generating an alert warning of the dangers associated with continuing the activity.

Similarly, the use of footwear items adapted for long-distance running mainly for a jumping activity may lead to the generation of an alert. Such an alert may be transmitted to a presentation computing device coupled to at least one connected sole.

Such warnings may be based on predetermined warning indicators and a function of shoe parameter values (e.g. cushioning, grip, . . . ).

Furthermore, the shoe parameter values 201 of a method 500 in accordance with the invention may include reference use parameters. In this case, the determination step 560 may be preceded by a step of identifying 550 a conventional and/or unconventional use implemented by the calculation computing device 30, said identification possibly including a comparison of the reference use parameters to the use parameter value calculated from the posture or mobility parameter values 301 for each connected sole 10.

A method 500 in accordance with the invention can further comprise a calculation step 570, implemented by a calculation computing device 30, of a global association index value from all the association index values previously determined for each connected sole 10. A method 500 in accordance with the invention may further comprise an identification step 580, implemented by a calculation computing device 30, of a trend, for a predetermined geographic area, from the global association index value correlated with the geographic parameter values 401 of the at least one connected sole 10.

A method in accordance with the invention may also include a step of correlation between the association index values of these users and the plantar morphology parameter values. Such correlations can be calculated as part of the learning model training. The plantar morphology parameter values of users can be obtained from dedicated servers or from information presentation devices coupled to the connected sole. The plantar morphology parameters may preferably correspond to one or more photographs of the foot or else to a three-dimensional model of the foot. These plantar morphology parameters may include dimensions of the foot (length/height of the arch, length/width of the foot), size and position of the toes, and/or shape of the arch of the foot (e.g. sunken or exaggerated for respectively flat foot or hollow foot).

Furthermore, a method according to the invention can be repeated for all the footwear items 11 of the same user. Thus, the method according to the invention may also include a step of analyzing the association indices generated for each of the footwear items 11 of a user. Furthermore, the method according to the invention can be configured to identify a footwear item more suited to the use of a user, for example according to his activities and the season. Advantageously, the method according to the invention will be able to identify the footwear item that tires the user the least.

The invention claimed is:

1. A system for analyzing the use of footwear items configured to determine an association index between use parameter values and shoe parameter values, comprising one or more calculation computing devices configured for:
    obtaining posture or mobility parameter values calculated from raw data generated by at least one connected sole of a footwear item;
    obtaining geographic parameter values, said geographic parameter values corresponding to a location of the at least one connected sole;
    obtaining shoe parameter values, said shoe parameter values comprising values of structural parameters, geometric parameters and/or aesthetic parameters of the footwear item including the at least one connected sole;
    calculating, for each connected sole, one or more use parameter values from the associated posture or mobility parameter values;
    determining, for each connected sole, an association index value between the associated use parameter value(s) and the associated shoe parameter values;
    calculating a global association index value from all the association index values previously determined for each connected sole; and
    identifying a trend, for a predetermined geographical area, from the global association index value correlated with the geographical parameter values of the at least one connected sole.

2. The system according to claim 1, wherein the one or more calculation computing devices is/are further configured to obtain plantar morphology parameter values of users of third-party connected soles, and wherein the association index values of these users are correlated with the plantar morphology parameter values.

3. The system according to claim 1, wherein the shoe parameter values include reference use parameters and the one or more calculation computing devices is/are further configured to identify a conventional and/or unconventional use, said identification including a comparison of the reference use parameters to the use parameter value calculated from the posture or mobility parameter values for each connected sole.

4. The system according to claim 1, wherein the geographic parameter values further include meteorological values.

5. The system according to claim 1, wherein the posture or mobility parameter values, the geographical parameter values, the shoe parameter values, the use parameter values and the association index values are associated with a unique identifier of the at least one connected sole.

6. The system according to claim 1, wherein the geographical parameter values are generated and transmitted to the one or more calculation computing devices, by the at least one connected sole.

7. The system according to claim 1, wherein the one or more calculation computing devices is/are further configured to identify a plurality of connected soles, each being associated with another footwear item having respective shoe parameters substantially identical to the shoe parameter values previously obtained.

8. The system according to claim 1, wherein the one or more calculation computing devices is/are further configured to identify a plurality of third-party connected soles, each being associated with another footwear item having respective posture or mobility parameters substantially identical to the posture or mobility parameter values previously obtained.

9. The system according to claim 1, wherein the one or more calculation computing devices is/are further configured to generate design parameters of the footwear item on the basis of the determined association index values between the use parameter values and the shoe parameter values.

10. The system according to claim 1, wherein the one or more calculation computing devices is/are further configured to generate production parameters relating to the manufacture of said footwear item on the basis of the determined association index values between the use parameter values and the shoe parameter values.

11. The system according to claim 1, wherein the one or more calculation computing device is/are further configured to generate values of logistics parameters relating to the manufacture and distribution of the footwear item on the basis of the geographical parameter values, the determined association index values between the use parameter values and the shoe parameter values.

12. The system according to claim 1, wherein the one or more calculation computing devices is/are further configured to receive wear parameter values of the footwear item associated with the connected sole and to generate production parameters relating to the manufacture of the footwear item on the basis of the determined association index values, shoe parameter values and wear parameter values.

13. A method for analyzing the use of footwear items to determine an association index between use parameters and shoe parameters, said method being implemented by a calculation computing device and comprising:
    obtaining posture or mobility parameter values calculated from raw data generated by at least one connected sole of a footwear item;
    obtaining geographic parameter values, said geographic parameter values corresponding to a location of the at least one connected sole;
    obtaining shoe parameter values, said shoe parameter values including values of structural parameters, geometric parameters and/or aesthetic parameters of the footwear item including the at least one connected sole;
    calculating, for each connected sole, one or more use parameter values from the posture or mobility parameter values;
    determining, for each connected sole, an association index value between the use parameter values and the shoe parameter values;
    calculating a global association index value from all the association index values previously determined for each connected sole; and
    identifying a trend, for a predetermined geographical area, from the global association index value correlated with the geographical parameter values of the at least one connected sole.

14. The method according to claim 13, wherein the shoe parameter values include reference use parameters, said method further comprising identifying a conventional and/or unconventional use, said identification including a comparison of the reference use parameters to the use parameter value calculated from the posture or mobility parameter values for each connected sole.

15. The method according to claim 13, wherein the posture or mobility parameter values have been calculated by one or more processors integrated into the at least one connected sole.

16. A system for analyzing the use of footwear items configured to determine an association index between use parameter values and shoe parameter values, comprising one or more calculation computing devices configured for:
- obtaining posture or mobility parameter values calculated from raw data generated by at least one connected sole of a footwear item;
- obtaining geographic parameter values, said geographic parameter values corresponding to a location of the at least one connected sole;
- obtaining shoe parameter values, said shoe parameter values comprising values of structural parameters, geometric parameters and/or aesthetic parameters of the footwear item including the at least one connected sole;
- calculating, for each connected sole, one or more use parameter values from the associated posture or mobility parameter values;
- determining, for each connected sole, an association index value between the associated use parameter value(s) and the associated shoe parameter values; and
- obtaining plantar morphology parameter values of users of third-party connected soles, and wherein the association index values of these users are correlated with the plantar morphology parameter values.

* * * * *